United States Patent [19]

Van Baelen

[11] 4,280,496
[45] Jul. 28, 1981

[54] PHLEBOTOMY NEEDLE ASSEMBLY

[75] Inventor: Armand R. Van Baelen, Rolling Meadows, Ill.

[73] Assignee: Baxter Travenol Laboratories, Inc., Deerfield, Ill.

[21] Appl. No.: 12,825

[22] Filed: Feb. 16, 1979

[51] Int. Cl.³ .............................................. A61M 5/00
[52] U.S. Cl. ............................... 128/214 R; 128/214.4
[58] Field of Search .......... 128/214 R, 214 C, 214 G, 128/214.2, 214.4, 221, 272.3

[56] References Cited

U.S. PATENT DOCUMENTS

| 2,137,132 | 11/1938 | Cooley | 128/276 |
|---|---|---|---|
| 2,647,514 | 8/1953 | Ellis | 128/275 |
| 3,057,350 | 10/1962 | Cowley | 128/214 G |
| 3,217,711 | 11/1965 | Pecina et al. | 128/214 C |
| 3,332,418 | 7/1967 | Brody | 128/214 G |
| 3,512,517 | 5/1970 | Kadish et al. | 128/214 R |
| 3,610,226 | 10/1971 | Albisser | 128/2 |
| 3,655,123 | 4/1972 | Judson et al. | 233/21 |
| 3,875,938 | 4/1975 | Mellor | 128/214.4 |
| 3,916,892 | 11/1975 | Latham | 128/214 R |
| 3,931,818 | 1/1976 | Goldowsky | 128/214 C |
| 4,048,995 | 9/1977 | Mittleman | 128/214.2 |
| 4,069,814 | 1/1978 | Clemens | 128/2 F |
| 4,086,924 | 5/1978 | Latham | 128/214 R |
| 4,096,860 | 6/1978 | McLaughlin | 128/214.4 |
| 4,113,627 | 9/1978 | Leason | 128/214 R |

FOREIGN PATENT DOCUMENTS 1187261 12/1957 France ................. 128/214 C

Primary Examiner—Kyle L. Howell
Assistant Examiner—T. J. Wallen
Attorney, Agent, or Firm—Paul C. Flattery; George Gerstman

[57] ABSTRACT

A phlebotomy needle assembly is provided which permits an anticoagulant to be mixed with whole blood immediately adjacent the cannula through which the whole blood is drawn, to prevent coagulation. A blood-anticoagulant mixing device has a blood inlet for coupling to the cannula; an anticoagulant solution inlet for coupling to a source of anticoagulant and a blood-anticoagulant mixture outlet for coupling to outlet tubing. The blood inlet and the anticoagulant inlet are generally coaxial and the mixture outlet is axially offset with respect to the inlets. The blood inlet defines a mixing chamber and a passage communicates with the mixing chamber and the mixing outlet for providing an outlet flow path through the mixing device for the blood-anticoagulant mixture.

11 Claims, 6 Drawing Figures

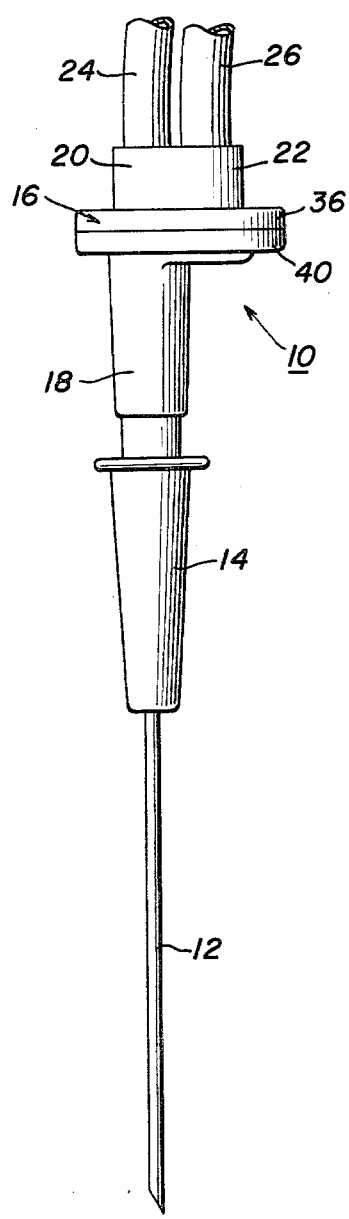
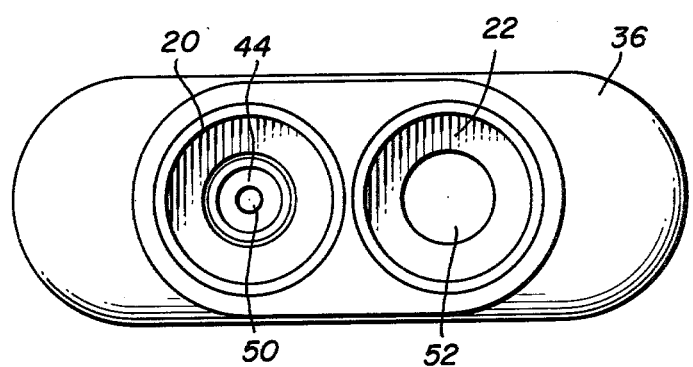
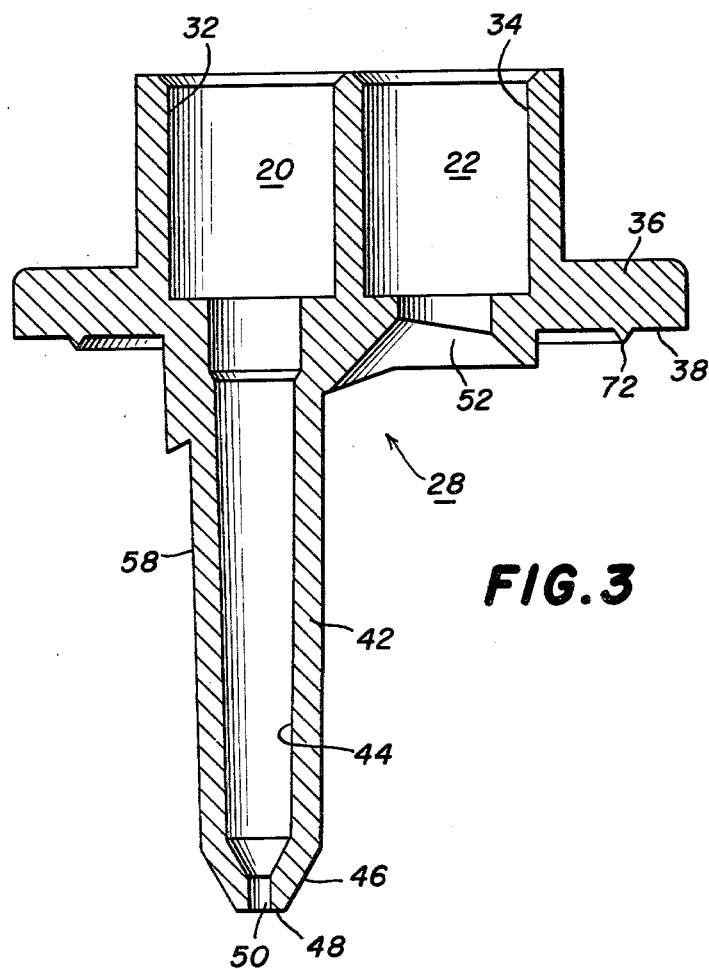

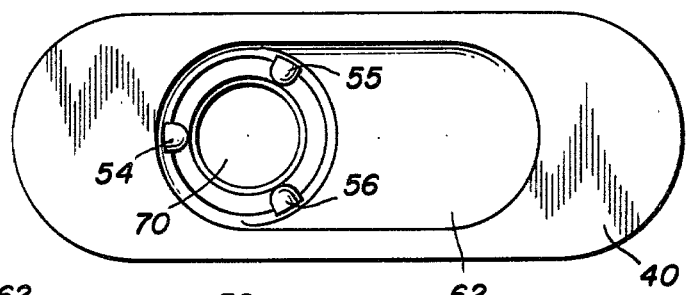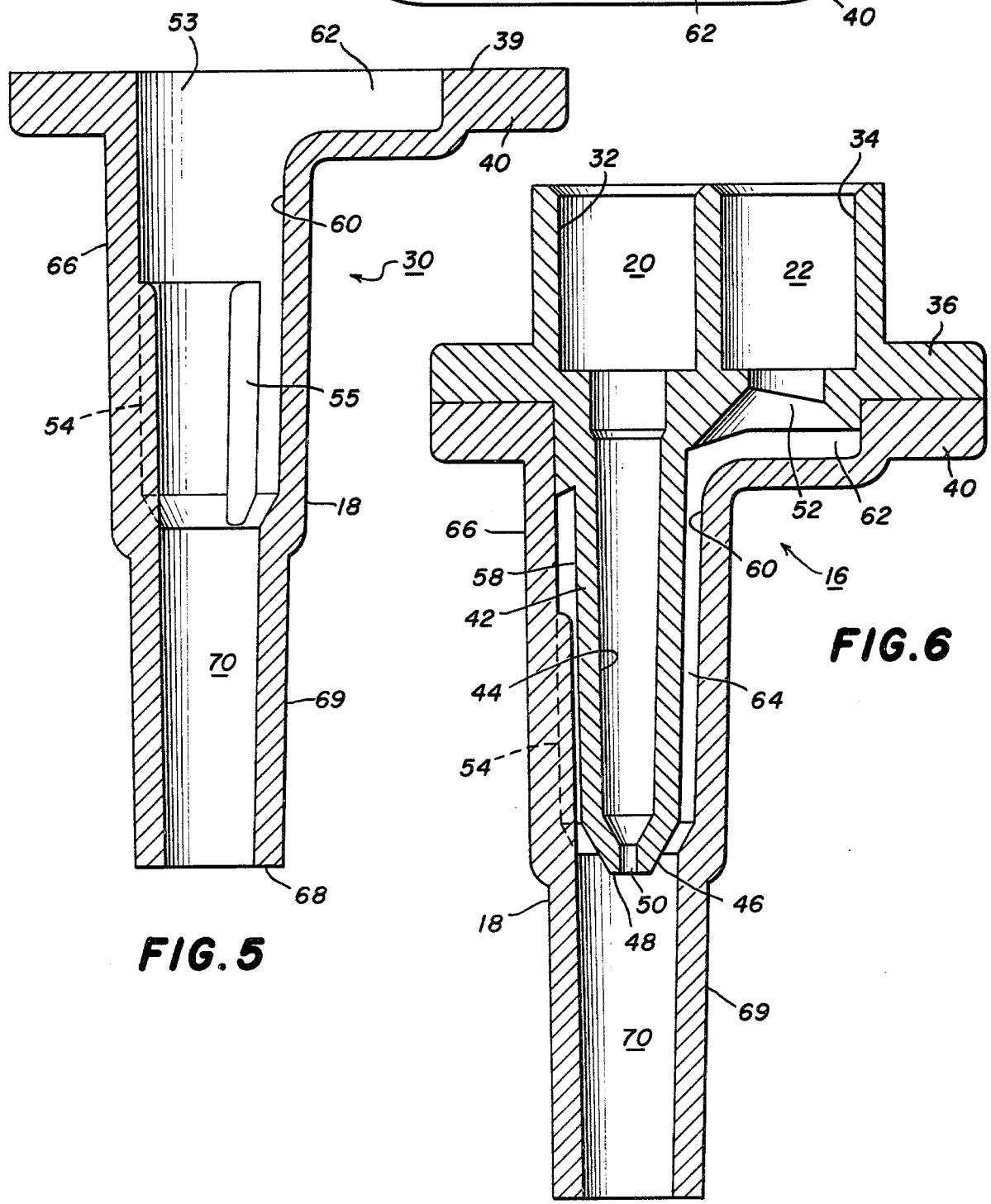

PHLEBOTOMY NEEDLE ASSEMBLY

BACKGROUND OF THE INVENTION

The present invention concerns a novel phlebotomy needle assembly, and, more particularly, a phlebotomy needle assembly through which whole blood is drawn and mixed with an anticoagulant.

In certain applications such as in cell separation techniques, whole blood is collected from the vein of a donor via a cannula and the whole blood is mixed with an anticoagulant solution such as ACD in order to prevent clotting of the whole blood. The ACD-whole blood mixture is then transmitted to appropriate separation equipment, such as centrifugal equipment or the like.

One widely used prior art anticoagulant-whole blood mixing system includes the cannula having a hub which is coupled to one end of flexible tubing carrying a roller clamp, with the other end of the flexible tubing being coupled to the bottom of a y-connector. One arm of the y is coupled to an anti-coagulant solution inlet line and the other arm of the y is coupled to an outlet tube for transmitting the anticoagulant-whole blood mixture. While the flexible tube carrying the roller clamp which couples the cannula to the bottom of the y connector may be relatively short, the configuration of the y connector and its distance from the cannula render possible some coagulation of the whole blood which is, of course, extremely undesirable.

It is, therefore, an object of the present invention to provide a phlebotomy needle assembly which allows mixing of an anticoagulant solution with the whole blood being withdrawn from the donor as close to the donor as possible.

Another object of the present invention is to provide a phlebotomy needle assembly that is simple in construction and easy to manufacture.

Other objects and advantages of the present invention will become apparent as the description proceeds.

SUMMARY OF THE INVENTION

In accordance with the present invention, a phlebotomy needle assembly is provided through which whole blood is drawn through a cannula and is mixed with an anticoagulant. The assembly includes a cannula extending from a hub and a blood-anticoagulant mixing device. The mixing device has a blood inlet for coupling to the hub, an anticoagulant solution inlet for coupling to a source of anticoagulant and a blood-anticoagulant mixture outlet for coupling to outlet tubing.

The improvement comprises the blood inlet and the anticoagulant inlet being generally coaxial and the mixture outlet being offset with respect to the inlets. The blood inlet defines a mixing chamber whereby the anticoagulant fed into the anticoagulant inlet enters directly into the mixing chamber to mix with the whole blood. A passage is defined by the mixing device and communicates with the mixing chamber and the mixing outlet for providing an outlet flow through the mixing device for the blood-anticoagulant mixture.

In the illustrative embodiment, the mixing device includes an upper portion comprising the anticoagulant inlet, the mixture outlet and an elongated member extending downwardly from the anticoagulant inlet. The elongated member defines a bore that is coaxial with the anticoagulant inlet. The mixing device also includes a lower portion comprising a housing for surrounding the elongated member and having the blood inlet extending downwardly from the housing. The mixing chamber comprises the volume defined by the blood inlet and located below the elongated member.

In the illustrative embodiment, the housing and the elongated member are spaced to define the passage between the housing and the elongated member. The elongated member forms a dispensing member and the blood inlet comprises a male luer for insertion into the cannula hub.

A more detailed explanation of the invention is provided in the following description and claims, and is illustrated in the accompanying drawings.

BRIEF DESCRIPTION OF THE DRAWINGS

FIG. 1 is an elevational view of a phlebotomy needle assembly constructed in accordance with the principles of the present invention;

FIG. 2 is a top plan view of the mixing device constructed in accordance with the principles of the present invention;

FIG. 3 is a cross-sectional elevation of the upper portion of the mixing device of FIG. 2;

FIG. 4 is a top plan view of the lower portion of the mixing device;

FIG. 5 is a cross-sectional elevation of the lower portion of the mixing device; and FIG. 6 is a cross-sectional elevation of the mixing device.

DETAILED DESCRIPTION OF THE ILLUSTRATIVE EMBODIMENT

Referring to the drawings, a phlebotomy needle assembly 10 is illustrated therein, including (with reference to FIG. 1) a needle cannula 12, a hub 14 to which the needle cannula is fixedly connected (as is well known in the art), and a mixing device 16.

Mixing device 16 includes a whole blood inlet 18, an anticoagulant inlet 20 and an anticoagulant-whole blood mixture outlet 22. Flexible plastic tubing 24 is connected to anticoagulant inlet 20 for feeding anticoagulant solution to mixing device 16 and flexible tubing 26 is connected to anticoagulant-blood mixture outlet 22 for transmitting the mixed blood and anticoagulant for further processing. Mixture device 16 is formed of an upper portion 28 (FIG. 3) which inserts into a lower portion 30 (FIG. 5) to form the assembled mixing device 16 (FIG. 6). Upper portion 28 includes anticoagulant inlet 20 at its top and anticoagulant-blood mixture outlet 22 also at its top and axially offset with respect thereto. Interior wall 32 of inlet 20 is sized to snugly receive tubing 24 which may be solvent bonded thereto, and interior wall 34 of outlet 22 is sized to snugly receive tubing 26 which may be solvent bonded thereto.

Upper portion 28 has a peripheral flange 36, the undersized 38 of which is adapted for connection to the top surface 39 of peripheral flange 40 of lower portion 30. An elongated member 42 extends downwardly from anticoagulant inlet 20 and defines a bore 44 which is coaxial with anticoagulant inlet 20. A taper 46 is provided adjacent the distal end 48 of elongated member 42 to form a more restricted orifice 50. The diameter of orifice 50 may be varied to change the velocity of anticoagulant entering chamber 70.

An opening 52 is provided below outlet 22 for coupling outlet 22 to a passage within the lower member as will now be described.

Referring to FIGS. 5 and 6, it is seen that lower member 30 defines an opening 53 for receiving elongated member 42 and carries three equally spaced longitudinal ribs 54, 55 and 56 which serves to space the external wall surface 58 of elongated member 42 from the internal wall surface 60 of lower portion 30. At the top of lower portion 30, a slot 62 is provided which communicates with opening 52 of upper portion 28 and which also communicates with a channel 64 which is defined between the external wall surface 58 of upper member 28 and internal wall surface 60 of lower member 30.

The external wall surface 66 of lower member 30 has a smaller diameter adjacent its distal end 68 for enabling the coupling of a cannula hub to wall 69. The diameter of wall 69 is such that wall 69 forms a male luer to snugly receive the cannula hub with a tight, frictional fit. As seen most clearly in FIG. 6, the inlet 80 defines a volume 70 below elongated member 42 which serves as a mixing chamber 70. Thus the anticoagulant solution which is introduced into inlet 20 will pass through the elongated member 42 and enter mixing chamber 70 where it will mix with the whole blood that is fed to mixing chamber 70 via cannula 12. The anticoagulant-blood mixture will pass via passage 64, slot 62 and opening 52 into outlet 22 and tubing 26. By reason of the aforesaid structure, it can be seen that mixing chamber 70 allows the mixing of the anticoagulant and the whole blood to occur as close as possible to the needle cannula outlet. This aids in preventing coagulation of the blood.

Mixing device 16 is preferably formed of an autoclavical plastic material. It can be seen that the mixing device 16 is formed in a two-piece construction, with the upper member 28 being connected to the lower member 30 by sonic weldng and utilizing a downwardly extending protuberance 72 (FIG. 3) utilized as is known in the art of sonic welding. After the top portion 28 is connected to the bottom portion 30 to form mixing device 16, tubes 24 and 26 are connected to inlet 20 and outlet 22, respectively.

Immediately prior to withdrawal of whole blood from a donor, a cannula 12 with attached hub 14 is pressure-fitted onto inlet 18. Tubing 24 is coupled to a suitable source of anticoagulant solution such as ACD and tubing 26 is coupled to suitable processing apparatus. Cannula 12 is inserted into the vein of the donor and mixing of the anticoagulant solution and the whole blood will occur within mixing chamber 70, and the mixed anticoagulant solution and whole blood will flow via tubing 26 as described previously.

Although an illustrative embodiment of the invention has been shown and described, it is to be understood that various modifications and substitutions may be made by those skilled in the art without departing from the novel spirit and scope of the present invention.

What is claimed is:

1. In a phlebotomy needle assembly through which whole blood is drawn through a cannula and mixed with an anticoagulant, and including a cannula extending from a hub; a blood-anticoagulant mixing device including an upper portion comprising an anticoagulant solution inlet for coupling to a source of anticoagulant and a blood-anticoagulant mixture outlet for coupling to outlet tubing, and an elongated member extending downwardly from said anticoagulant inlet said elongated member defining a bore that is coaxial with said anticoagulant inlet; a lower portion comprising a housing for surrounding said elongated member and a blood inlet for coupling to said hub, said inlet extending downwardly from said housing; said upper portion and said lower portion being initially separable; said mixture outlet being offset with respect to said inlets; said blood inlet defining a mixing chamber whereby the anticoagulant solution fed into the anticoagulant inlet enters directly into the mixing chamber to mix with the whole blood, said mixing chamber comprising the volume defined by said blood inlet and located below said elongated member; a passage defined by said mixing device and communicating with said mixing chamber and said mixing outlet for providing an outlet flow path through said mixing device for the blood-anticoagulant mixture; and a radially extending flange extending from said upper portion and a radially extending flange extending from said lower portion, and means connecting the bottom of said upper flange portion to the top of said lower flange portion.

2. An assembly as described in claim 1, said housing and said elongated member being spaced to define said passage therebetween.

3. An assembly as described in claim 1, said elongated member comprising a dispensing member for dispensing the anticoagulant into said mixing chamber.

4. An assembly as described in claim 1, said connecting means comprising a sonic weld.

5. An assembly as described in claim 1, said anticoagulant inlet and said mixture outlet each comprising openings defined by the top of said mixture device for snugly enclosing the ends of flexible plastic tubing.

6. An assembly as described in claim 1, said housing carrying means on its internal wall for spacing said elongated member therefrom to define said passage between said housing and said elongated member.

7. An assembly as described in claim 6, said spacing means comprising a plurality of longitudinal ribs.

8. In a phlebotomy needle assembly through which whole blood is drawn through a cannula and mixed with an anticoagulant, and including a cannula extending from a hub; a blood-anticoagulant mixing device having a blood inlet for coupling to said hub, an anticoagulant solution inlet for coupling to a source of anticoagulant and a blood-anticoagulant mixture outlet for coupling to outlet tubing, the improvement comprising:

said mixture device including an upper portion comprising said anticoagulant inlet, said mixture outlet and an elongated member extending downwardly from said anticoagulant inlet; said elongated member defining a bore that is coaxial with said anticoagulant inlet;

said mixing device including a lower portion comprising a housing for surrounding said elongated member and having said blood inlet extending downwardly from said housing;

said blood inlet and said anticoagulant inlet being generally coaxial;

said mixture outlet being axially offset with respect to said inlet;

said blood inlet defining a mixing chamber whereby the anticoagulant solution fed into the anticoagulant inlet enters directly into the mixing chamber to mix with the whole blood;

said housing carrying means on its internal wall for spacing said elongated member therefrom to define a passage between said housing and said elongated member, said passage communicating with said mixing chamber and said mixing outlet for providing an outlet flow path through said mixing device for the blood-anticoagulant mixture; and said anticoagulant inlet and said mixture outlet each comprising openings defined by the top of said mixture device for snugly enclosing the ends of flexible plastic tubing.

9. An assembly as described in claim 8, said elongated member comprising a dispensing member for dispensing the anticoagulant into said mixing chamber.

10. An assembly as described in claim 8, said upper portion including a radially extending peripheral flange and said lower portion including a radially extending peripheral flange, and means connecting the bottom of said upper portion flange to the top of said lower portion flange.

11. An assembly as described in claim 10, said connecting means comprising a sonic weld.

* * * * *